United States Patent [19]

Chang

[11] Patent Number: 4,822,470

[45] Date of Patent: Apr. 18, 1989

[54] METHOD OF AND APPARATUS FOR CELL PORATION AND CELL FUSION USING RADIOFREQUENCY ELECTRICAL PULSES

[75] Inventor: Donald C. Chang, Houston, Tex.

[73] Assignee: Baylor College of Medicine, Houston, Tex.

[21] Appl. No.: 106,282

[22] Filed: Oct. 9, 1987

[51] Int. Cl.[4] .......................... C12N 5/00; B01D 57/02
[52] U.S. Cl. ................................. 204/299 R; 435/89; 435/172.1; 435/172.2; 435/173
[58] Field of Search .................. 435/173, 172.1, 172.2, 435/94, 89, 90-95; 204/181.1, 299 R

[56] References Cited

U.S. PATENT DOCUMENTS

| | | | |
|---|---|---|---|
| 4,441,972 | 4/1984 | Pohl | 204/183.1 |
| 4,452,747 | 6/1984 | Gersonde | 264/4.1 |
| 4,476,004 | 10/1984 | Pohl | 204/299 R |
| 4,524,079 | 6/1985 | Hofmann | 426/234 |
| 4,561,961 | 12/1985 | Hofmann | 204/299 R |
| 4,578,167 | 3/1986 | Schoner | 204/183.1 |
| 4,578,168 | 7/1984 | Hofmann | 204/299 R |
| 4,623,302 | 11/1986 | Sowers | 435/172.2 |
| 4,661,451 | 4/1987 | Hansen | 435/174 |
| 4,665,898 | 5/1987 | Costa | 128/1.3 |

FOREIGN PATENT DOCUMENTS

86/02377  4/1986  World Int. Prop. O. .......... 435/173

OTHER PUBLICATIONS

Schwan et al., "Alternating Current Field-Induced Forces and Their Biological Implications", J. Electchem. Soc'y, vol. 116, pp. 22C-25C, (1969).
Zimmerman et al., "Electric Field-Induced Cell-To-Cell Fusion", J. Membrane Biol., vol. 67, pp. 165-182, (1982).
Stenger et al., "Kinetics of Ultrastructural Changes During Electrically Induced Fusion of Human Erythrocytes", J. Membrane Biol., vol. 93, p. 44, (1986).
Chemical Abstract, vol. 97, #210964w, p. 375, (1982).
Proceedings of International Symposium on Molecular Mechanisms of Membrane Fusion, Chang, D. C. and Hunt, J. R., p. 26, (1987).
Cell Fusion ed. by A. E. Sowers, "Electrofusion and Plant Somatic Hybridization", Bates, G. W., Nea, L. J. and Hasenkampf, C. A., Plenum Press, N.Y., pp. 479-496, (1987).
Cell Fusion by A. E. Sowers, "Microinjection of Culture Cells via Fusion with Loaded Erythrocytes", Schlegel, R. A. and Lieber, M. R., Plenum Press, N.Y., pp. 457-479, (1987).
Cell Fusion ed. A. E. Sowers, "Electrofusion Principles and Applications", Bates, G. W., Saunders, J. A. and Sowers, A. E., Plenum Press, N.Y., pp. 367-395, (1987).
J. Membrane Biol., Stenger, D. A. and Hui, S. W., 93:43-53, (1986).
J. Cell Biology, Sowers, A. E., 102:1358-1362, (1986).
Exp. Cell Res., Kubiac, J. Z. and Tarkowski, A. K., 157:561-566, (1985).

(List continued on next page.)

Primary Examiner—John F. Niebling
Assistant Examiner—Rodriques, Isabelle
Attorney, Agent, or Firm—Fulbright & Jaworski

[57] ABSTRACT

Disclosed are an apparatus and a method for the poration and fusion of cells using radiofrequency electrical pulses. The electrodes of the apparatus can be hand held or part of integrated equipment with special containers for cells. The electrodes, which are positioned equal distance from each other, are attached to a power function generator. The power function generator can apply a continuous AC electrical field and/or a pulsed radiofrequency electrical field across the electrodes. The alternating electrical field induces cell dielectrophoresis. The pulsed radiofrequency electrical field porates or fuses the cells. The method can be used to fuse or porate a variety of cells including erythrocyte ghosts, liposomes, vesicles, isolated cells and cultured cells. During the poration or fusions a variety of chemical agents including antibodies, proteins, drugs, molecular probes, hormones, growth factors, DNA, RNA, enzymes, organic chemicals and inorganic chemicals can be introduced into these cells. The method can also be used to produce new species and to make hybridoma cells which produce monoclonal antibodies.

24 Claims, 6 Drawing Sheets

OTHER PUBLICATIONS

Nature, Lo et al., 310:794–796, (1984).
Arch. Microbiol., Halfmann, H. J., Emeis, C. C. and Zimmermann, U., 134:1–4, (1983).
J. Membrane Biol., Holzapfel, C., Vienken, J. and Zimmermann, U., 67:13–26, (1982).
Science, Tesissie, J., Knutson, V. P., Tsong, T. Y. and Lane, M. D., 216:537–538, (1982).
J. Membrane Biology, Zimmermann, U., Vienken, J., 67:165–182, (1982).
J. Cell Biology, White., J. Matlin, K. and Helenius, A., 89:674–679, (1981).
Biochimica et Biophysica Acta, Zimmermann, U. and Scheurich, P., 641:160–165, (1981).
J. Biol. Phys., Pohl, H. A., Kaler, K. and Pollock, K., 9:67–86, (1981).
Bioelectrochemistry and Bioenergenics, 7:553–574, (1980), or J. Electroanal. Chem., 116:553–574, (1980), Zimmermann, U., Vinken, J., Pilwat, G.
Naturwissenschaften, Neuman, E., Gerisch, G. and Opatz, K., 67:414–415, (1980).
Nature, Galfre, G., et al., 266:550–552, (1977).
Somatic Cell Genetics, Davidson, R. L., O'Malley, K. A. and Wheeler, T. B., 2:271–280, (1976).
J. Electrochem Society, Schwan, H. P. and Sher, L. D., 116:22C–26C, (1969).

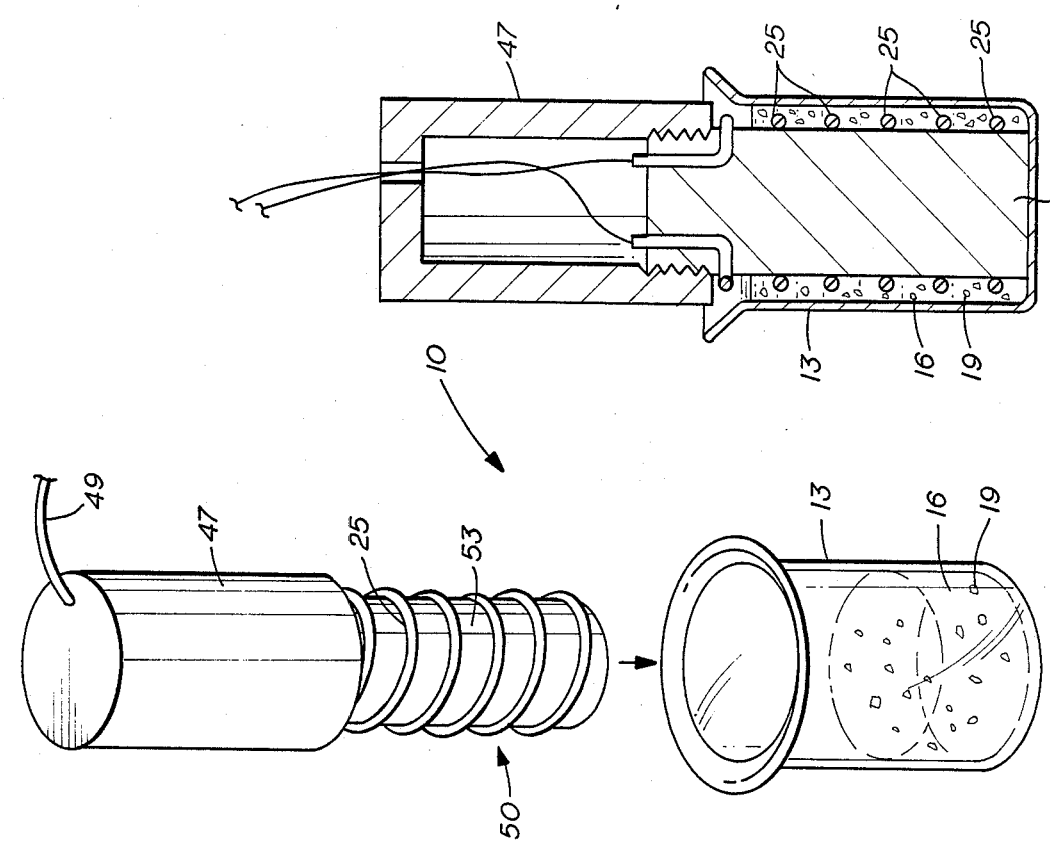
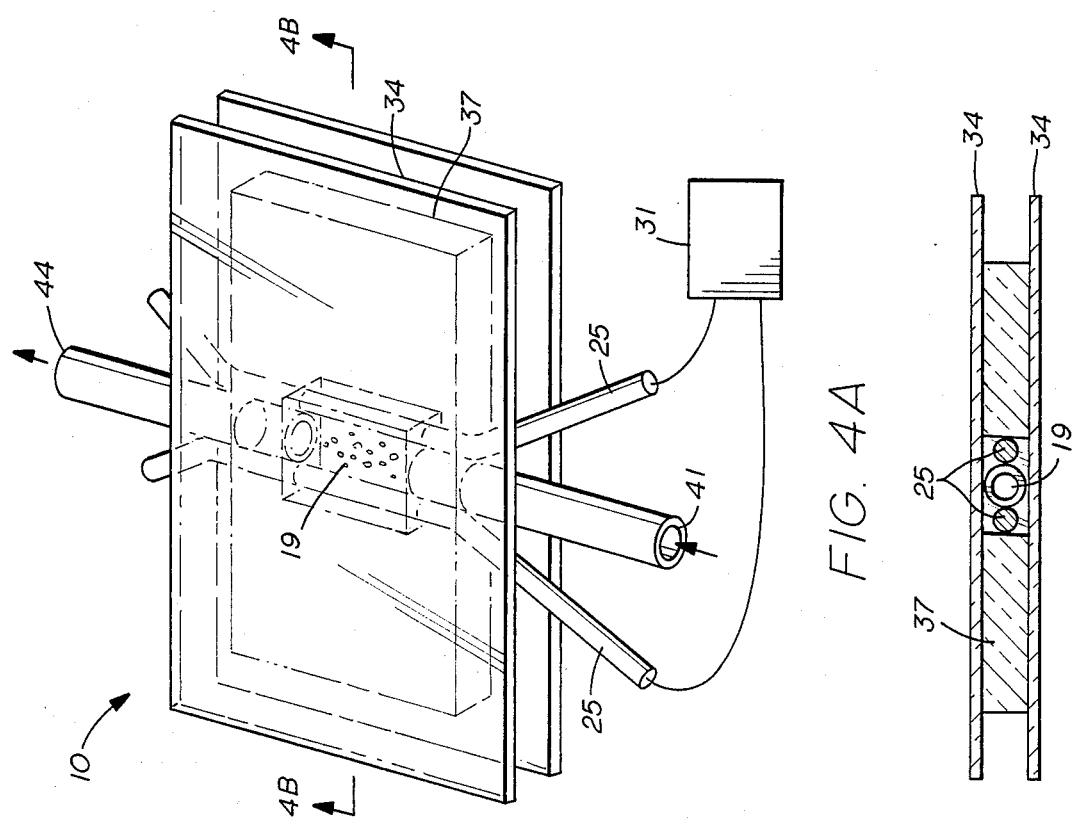

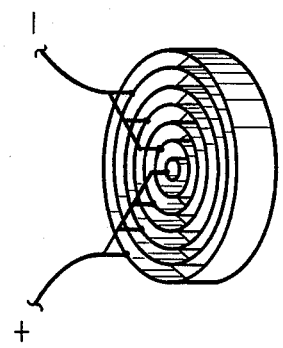
FIG. 11A
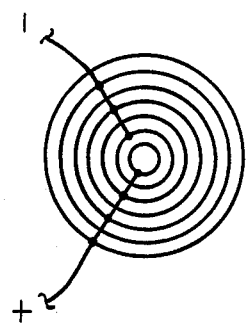
FIG. 11B
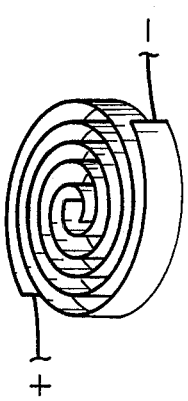
FIG. 10A
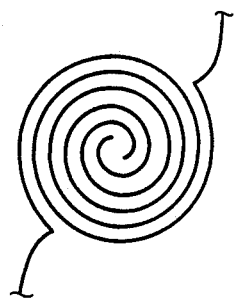
FIG. 10B
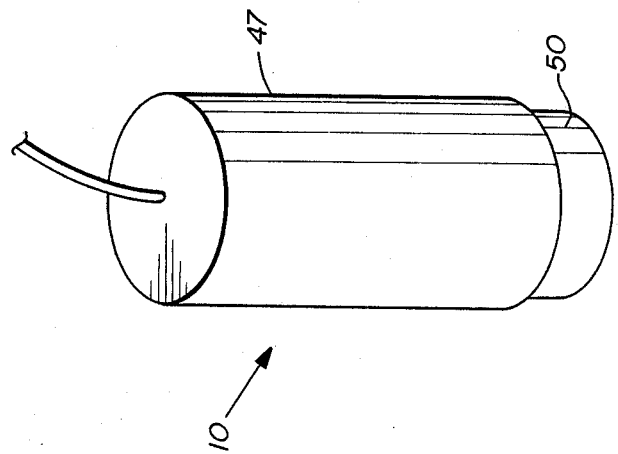
FIG. 9
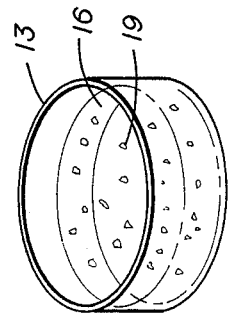

METHOD OF AND APPARATUS FOR CELL PORATION AND CELL FUSION USING RADIOFREQUENCY ELECTRICAL PULSES

FIELD OF THE INVENTION

This invention relates to the field of poration and fusion of biological cells by application of a high-power pulsed radiofrequency electric field which produces a localized sonication effect in the cell membrane.

BACKGROUND

Cell fusion plays a very important role in modern biotechnology. For examples, one key procedure in genetic engineering is the introduction of exogenous genetic material into a host cell. This insertion of genes is accomplished by either permeabilizing the cell membrane to allow entry of genetic material or fusing the host cell with a cell containing the desired genetic material. Cell fusion is also important in the production of monoclonal antibodies. The process of producing monoclonal antibodies requires the fusion of antibody producing cells with continuously dividing cancer cells. (Galfre, G. et al., Nature 266:550–552 (1977); Lo, M. M. S. et al., Nature 310:794–796 (1984)). Additionally, one highly effective method of delivering those drugs which normally cannot enter a cell is to fuse the cell with liposomes or red blood cell ghosts that have been pre-loaded with specific drugs. (Schlegel & Lieber, *Cell Fusion*, ed by A. E. Sowers, Plenum Press (1987)).

The conventional techniques of cell fusion rely mainly on the actions of viruses (White, J. et al., J. Cell Biol. 89:674–679 (1981)); or chemical agents such as polyethylene glycol, (Davidson, R. L. et al., Somatic Cell Genetics 2:271–280 (1976)). Virus-induced and chemical-induced fusion methods have many shortcomings. Not only is the fusion yield often very poor, typically less than 0.01%, but the standard fusion techniques may also cause severe side effects on the fused cells; thus greatly limiting their usefulness for many systems.

Alternative methods which induce cell fusion and cell poration by electric fields have been developed. (Pohl, U.S. Pat. Nos. 4,476,004; Sowers, 4,622,302; Schoner, 4,578,167; Neumann, E. et al. Naturwissenschaften 67:414–415 (1980); Zimmerman, U. and Nienken, J., J. Membrane Biol. 67:165–182 (1982); Bates G. W., et al., *Cell Fusion*, Plenum Press N.Y. pp. 367–395 (1987)). The basic principle of these methods of electrofusion is to apply a pulsed high strength direct-current (DC) electric field across the cell. This DC field is usually generated by briefly switching on a DC power source or by discharging a capacitor. The applied DC field has a strength of several kilovolts per centimeter. This external electric field induces a large cell membrane potential. When the membrane potential is of sufficient magnitude, a reversible breakdown of a small area of the cell membrane occurs. The breakdown results in the formation of physical pores at the surface of the cell. This process is called electroporation. Intracellular and extracellular material can exchange through the pore while it is open. After the DC field is removed, the pore will normally reseal quickly. When a pore is created between two closely adjacent cells a cytoplasmic bridge is formed via the pore. When the DC field is turned off the pore cannot reseal. Instead, the cytoplasmic bridge usually begins to enlarge, eventually causing the two cells to fuse.

Although the DC electrofusion method has been used successfully for a number of biological cells, including plant protoplasts, (Zimmerman U. et al., Biochem. Biophys. ACTA 641:160–165 (1981); Bates G. W. et al., *Cell Fusion*, Plenum Press pp. 479–496 (1987)); blood erythrocytes (Sowers, A. E., J. Cell. Biol. 102:1358–1362 (1986); Chang and Hunt, *Proceedings of the International Symposium on Molecular Mechanisms of Membrane Fusion*, Buffalo, New York pp. 26 (1987); Stenger D. A. and Hui S. W., J. Membrane Biol. 93:43–53 (1986)); tumor cells, (Lo M. M. S. et al., Nature 310:794–796 (1984); Tessie, J., et al., Science 216:537–538 (1982)); yeast cells, (Halfmann, H. J., et al., Archiv. Microbiol. 134:1–4 (1983)); blastomerers and eggs, (Kubiac, J. Z. and Jarkowski, A. K., Exp. Cell Res. 157:561–566 (1985)), there are still many limitations to the use of this method. First, not all cell types can be fused with the same ease. In fact many cell types are extremely difficult to fuse with DC pulses. Second, there are many unknown factors which influence fusion yield. Fusion of certain cell types may be successful in one laboratory but not in others. The DC pulse method is still more of an art than a well understood procedure. Third, it is very difficult to use the DC pulse method to fuse cells of different sizes. This later problem occurs because the membrane potential induced by the external DC field is proportional to the diameter of the cell. Thus the induced potential is larger for bigger cells. It is nearly impossible to chose a proper field strength of external field in order to fuse cells of two different sizes. When the external field is just sufficient to cause membrane breakdown in the larger cell, it is inadequate to induce a critical membrane potential in the smaller cell. On the other hand, if the external field is elevated to cause a membrane breakdown in the small cell, the large potential induced in the larger cell will cause an irreversible membrane breakdown and destroy the cell.

The present invention provides an improved method of cell poration and cell fusion which overcomes the above problems. Unlike the conventional electrofusion method which employs DC pulses to induce membrane breakdown, the present invention uses a pulse or pulses of radio-frequency (RF) electric field to reversibly permeabilize cells and induce cell fusion. Breakdown in the cell membrane is caused by a localized sonication induced from the RF field. Such localized sonications are more effective in breaking down the cell membrane than a DC field. Since this new method uses only physical means (i.e. radio frequency energy) to induce cell poration and cell fusion, it is free of biological or chemical contamination. The present invention produces results in seconds, provides much higher yields than conventional methods, and has minimal biological side effects. Thus it is a clean, fast, efficient and safe method.

SUMMARY OF THE INVENTION

An object of the present invention is a method for the poration of cells.

An additional object of the present invention is a method for the fusion of cells.

A further object of the present invention is a device for the poration and fusion of cells.

Another object of the present invention is a method for the formation of hybridoma cells by the fusion of cells with radiofrequency electric field.

An additional object of the present invention is a method which greatly enhances the efficiency of producing monoclonal antibodies.

Another object of the present invention is the formation of a new species by the fusion of cells from different species using high power RF pulses.

An additional object of the present invention is the introduction of chemicals and biological molecules into cells by the procedures of poration and/or fusion.

Thus in accomplishing the foregoing objects there is provided in accordance with one aspect of the present invention a method for poration of biological particles comprising the steps of placing a plurality of biological particles in solution between two electrodes and applying a high-power pulsed radiofrequency oscillating field across the electrodes for porating the particles. The biological particles can either be suspended cells in solution or attached cells in cell culture. An additional embodiment of this method includes fusing the biological particles by placing the suspended biological particles in a container which allows the biological particles to congregate before applying the pulsed radio-frequency field.

An alternative method includes fusing the biological particles by applying a low power (e.g., 100 to 400 V/cm) alternating (AC) electrical field before and/or after the pulsed radiofrequency oscillating field. The low-power electric field can cause the particles to move dielectrophoretically to form "pearl chains".

The biological particles can be a variety of materials including biological cells, liposomes, vesicles, and erythrocyte ghosts.

The pulsed radiofrequency field applied for the poration and fusion of cells can be an oscillating field of a single frequency or a mixed frequency. The radiofrequency oscillating field may be in the frequency range of 50 KHz to 500 MHz with a pulse width of about 1 $\mu$sec to 10 msec and a pulse amplitude of up to about 15 KV/cm. In a preferred embodiment the radiofrequency oscillating field is about 0.1 to 10 MHz and the pulse width is about 20 to 200 $\mu$sec and the pulse amplitude is about 5 KV/cm.

Another aspect of the present invention is the fusion of cells for the formation of new species, the introducing of chemical agents and natural or man-made genetic material into cells, and the formation of hybridoma cells. By the appropriate selection of cell types and materials new species can be formed either by the combining of genetic material from two different species by the fusion of their cells, or by the isolation or synthesis of the genetic material, the introduction of the genetic material into cells and then fusion. Hybridoma cells are made by the fusion of antibody producing cells with continuously dividing cancer cells. Chemicals, drugs, DNA, RNA and other molecules can be introduced into cells by preloading vesicles, liposomes or erythrocyte ghosts before fusion with target cells.

Another aspect of the present invention is a device for the poration or fusion of biological particles comprising a container of non-conducting material capable of holding liquid and including an access port for receiving the biological particles. The device also includes electrodes positioned equidistant from each other and inserted into the container. A high-power function generator is attached to the electrodes and is capable of generating a radiofrequency electric field and/or an alternating electric field. In one embodiment the container is shaped to allow the biological particles to congregate.

An additional aspect is a device for poration and fusion of biological particles comprising a glass chamber and used with an optical microscope for observation of the poration and fusion of cells.

A further aspect is a cell poration and fusion device which can be hand held. This device includes a handle and equidistant electrodes. The electrodes can be side-attached or bottom-attached and can be designed in a variety of shapes including rings, circles, double helices, squares, ellipses, concentric rings, concentric squares, interdigitating arrays, spirals and parallel plates.

Other and further objects, features and advantages will be apparent from the following description of the presently preferred embodiments of the invention given for the purpose of disclosure when taken in conjunction with the accompanying drawings.

BRIEF DESCRIPTION OF THE DRAWINGS

The invention will be more readily understood from a reading of the following specification by reference to accompanying drawings, forming a part thereof, where examples of embodiments of the invention are shown and wherein:

FIG. 4 is a schematic of a chamber for cell poration and/or cell fusion for optical microscopic observation. 4A is a elevational view of the chamber and 4B is a cross-sectional view of the chamber.

FIG. 5 is a schematic of a hand held device for cell poration and/or cell fusion using a side contact configuration. 5A shows an elevational view of the device and 5B shows a cross-sectional view of the electrode inserted inside the cell container.

FIG. 9 is a schematic of a cell fusion and cell poration device with a bottom-contact configuration of electrodes.

FIG. 10 is a schematic of the double spiral design for the bottom contact electrode assembly. 10A shows a elevational view and 10B shows top view of the electrode.

FIG. 11 is a schematic view of a concentric ring design for the bottom contact electrode assembly. 11A shows an elevational view and 11B shows a top view of the electrode.

DETAILED DESCRIPTION

In the description which follows like parts are marked throughout the specifications and drawings with the same referenced numerals. The drawings are not necessarily to scale and certain features of the invention may be exaggerated in scale or shown in schematic form in the interest of clarity and conciseness. It will be readily apparent to one skilled in the art that various substitutions and modifications may be made to the invention disclosed herein without departing from the scope and spirit of the invention.

Figure 1A:
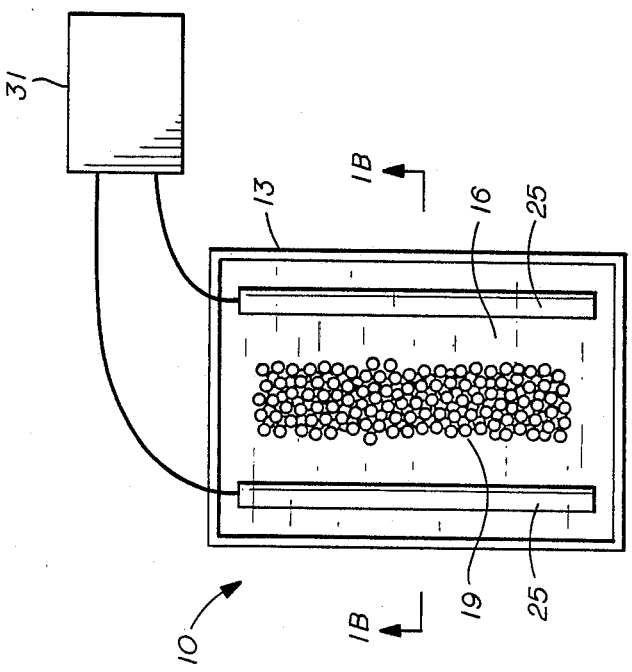
FIG. 1 is a schematic of one form of the present invention using a chamber which allows for the congregation of cells by gravity. 1A is a top view of the device and 1B is a cross-sectional view of the device showing the fusion chamber.
Figure 1B:
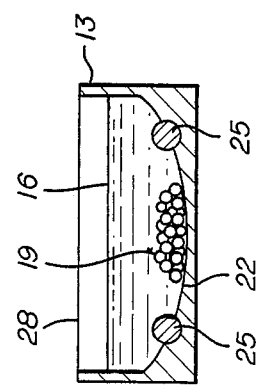

One embodiment comprises a method for poration of biological particles comprising the steps of placing the biological particles in solution between two electrodes and applying a pulsed radiofrequency (RF) oscillating field across the electrodes, FIG. 1. A variety of biological particles can be used including biological cells, vesicles, erythroycte ghosts and liposomes. The biological particles can be suspended cells in solution or can be attached cells in cell culture.

When a cell is placed in an electric field, an electrical potential is induced across the cell membrane. For a spherical cell, the membrane potential induced by an external electric field is $$V_m = 1.5 \, rE \cos \theta \qquad (1)$$

where r is the radius of the cell, E is the strength of the external field and $\theta$ is the angle between the direction of the external field and the normal vector of the membrane at the specific site.

The induced electric field within the membrane is $$E_m = V_m/d = 1.5 \, (r/d) \, E \cos \theta \qquad (2)$$

where d is the thickness of the membrane. Since d is much smaller than r (d is about $6 \times 10^{-7}$ cm while r is in the order of several microns), $E_m$ is about 1000 fold larger than the applied field, E. The large electric field within the membrane produces two effects. First, it exerts a strong force on the phosphate head group of the lipid molecules in the membrane and tends to move them in the direction of the field. Secondly, it compresses the membrane. When the external electric field oscillates, the lipid molecules within the membrane also undergo an oscillating motion.

In this arrangement, the cell itself functions as an antenna and the membrane is a transducer which converts the electrical oscillation into a mechanical oscillation. Thus, it is possible to generate an ultrasonic motion in the cell membrane by applying an external RF field. Because the induced potential at a given site of the membrane is a function of the angle between the orientation of the membrane and the electric field vector, the induced potential is not uniform over the entire cell surface. The applied energy is focused at the poles of the cell, that is, at $\theta = 0°$ or 180°. Because the amplitude of the external field can be adjusted such that there is sufficient sonication power to break down the cell membrane at the poles but not at other parts of the membrane, the sonication can be localized. Experiments indicated that this localized membrane breakdown induced by the externally applied pulsed RF field is reversible. That is, the pore(s) induced by the RF field reseal quickly (within one minute) after the field is turned off. Furthermore, most of the cells apparently stay viable.

Such temporary permeabilization of the cell membrane is called cell poration. During this time period when pores are formed a brief exchange of intracellular and extracellular materials occur. Many molecules, including drugs, antibodies, and gene segments, which normally cannot penetrate the cell membrane, can enter the cell through the temporarily opened pores that were induced by the pulsed RF field.

Another embodiment of this invention comprises a method for fusing cells. In order for biological particles to be fused, they must be in close proximity. When cells are in close proximity they are said to congregate. Two alternative procedures may be used to congregate the cells before fusion. In one, a container with a shape that allows the biological particles to congregate by gravity is used. For example, the bottom of the container can be made in a concave shape (see FIGS. 1 and 3). This allows the cells to congregate. When the cell membranes are permeabilized by the applied RF field, the closely adjacent cells can form cytoplasmic bridges, this process results in the fusion of cells.

Alternatively, a low amplitude continuous alternating current (AC) electrical field can be applied across the two electrodes. The frequency ranges from about 60 Hz to about 10 mega Hz. Typically a 100–400 V/cm field strength is used. Under the low amplitude AC field the cells act as dipoles and line up parallel to the field, eventually forming a long chain of cells which appear like "pearl chains". This process is called "dielectrophoresis" (Schwan, H. P. and Sher, L. D., J. Electrochem. Soc. 116:22C–26C (1969); Phol, H. A., et al., J. Biol. Phys. 9:67–86 (1981)). Formation of this pearl chain normally takes about a few seconds to one minute.

The present invention uses a pulsed RF field to porate and/or fuse cells and has a clear advantage over the conventional electro-fusion method that uses a pulsed DC field. First, the radiofrequency field is a much more efficient means of transmitting energy to the cell membrane than the direct current field. The present invention utilizes a localized sonication to break down the cell membrane. This method is much more effective than the DC pulse method which relies solely on the electrical breakdown. The cell membrane is composed of macromolecules which have characteristic frequencies of thermal motion. When the frequency of the applied oscillating field matches one of these natural frequencies, a condition of resonance is reached, and the efficiency of energy transfer is greatly enhanced. In real biological cells the resonance peak can be very broad. The pulsed radiofrequency field can be carefully varied to achieve the proper resonant frequency for the cells of interest. Consequently, the ability to induce membrane breakdown will require less power than using a direct current field and result in less risk of irreversibly damaging the cell.

Second, this invention overcomes the difficulties encountered when the conventional methods are used to fuse cells of different size. In order to produce an electrical breakdown of the cell membrane, the field-induced membrane potential must exceed a certain critical value, $V_c$ (typically 1 volt). Such breakdown can be reversible, and the membrane will reseal after the external field is turned off if the induced membrane potential is not too much larger than $V_c$. The cell normally remains viable after such reversible breakdown. On the other hand, if the induced potential is much higher than $V_c$, the membrane breakdown is irreversible, the cell is permanently damaged, and will not remain viable.

From Eq. 1 it can be seen that when cells of different sizes are placed inside an electric field, the induced membrane potential is higher for the larger cell than for the smaller cell. This size-dependence of membrane potential causes a problem when attempting to fuse cells of different sizes using a DC field. Assume that two cells, A and B, are to be fused and that the radius of cell A, $r_a$, is about twice as big as the radius of cell B, $r_b$. In order to cause a reversible membrane breakdown in cell B, the applied external field must be sufficient so that 1.5 E $r_b$ is greater than $V_c$. The same applied electric field will induce a much larger $V_m$ in Cell A. Thus $V_m$ will be very much greater than $V_c$, and will cause an irreversible breakdown of the membrane leading to damage to cell A. Thus it is very difficult to use direct current pulses to fuse cells of significantly different sizes.

This problem can be solved by applying a pulsed radiofrequency field. When the applied field is a radiofrequency oscillating field instead of a DC field, the amplitude of the induced membrane potential is a function of the frequency. The membrane potential predicted in Eq. (1) is derived under the steady state condition. The induced potential does not arise instantaneously upon the application of the external field. If the external field is stationary, the membrane potential will reach $V_m$ given a sufficient time. The time required to establish this steady state membrane potential is called "relaxation time", or $\tau$, which is given by $$1/\tau = 1/R_m C_m + 1/rC_m(R_i + 0.5R_e) \quad (3)$$

where $R_m$ and $C_m$ are specific resistance and specific capacitance of the membrane, and $R_i$ and $R_e$ are the specific resistances of the intracellular medium and the extracellular medium, respectively. (C. Holzapfel et al., *J. Membrane Biol.*, 67:13-26 (1982)). For a cell of several microns in diameter, $\tau$ is typically less than 1 $\mu$sec.

Since $R_m$ in most cells is very large, for practical purposes, eq. (3) can be simplified to $$\tau = rC_m(R_i + 0.5R_e) \quad (4)$$

Thus the relaxation time is approximately proportional to the radius of the cell.

Because the build-up of the membrane potential requires a time period characterized by the relaxation time $\tau$, the membrane potential induced by a RF field is frequency dependent. If a radiofrequency field is applied at a frequency smaller than $1/\tau$, the membrane potential has no problem in following the external field. The applied field will produce a 100% cellular response in $V_m$. On the other hand, if the frequency of the applied radiofrequency field is greater than $1/\tau$, the membrane potential cannot catch up with the changes in the applied field, and the response of the membrane potential will be less than 100%. In general, the maximum membrane potential induced by a RF field is $$V(\omega) = 1.5 \; rE \cos \theta X(\omega) \quad (5)$$

where r, E and $\theta$ have the same meaning as in Eq. (1), $\omega$ is the angular frequency, and $X(\omega)$ is a function of the frequency such that $$X(\omega) = \frac{1}{\sqrt{1 + (\omega\tau)^2}} \quad (6)$$

when $\omega < 1/\tau$, $X(\omega)$ is near unity. When $\omega > 1/\tau$, $X(\omega)$ decreases very rapidly with increasing frequency.

This frequency dependent effect can be used to fuse cells of different sizes. From Eq. (4), $\tau$ of the cell is roughly proportional to r. Thus the larger cell will have a longer $\tau$. To fuse the A and B cells a pulsed RF electric field that has a frequency w is applied such that $$1/\tau_a < \omega < 1/\tau_b \quad (7)$$

Since the frequency is less than $1/\tau_b$, $X(\omega)$ approaches unity for cell B and thus the field will produce a full effect on the small cell. On the other hand, since the frequency is greater than $1/\tau_a$, the induced membrane potential in cell A cannot fully follow the variation of the applied field, that is, $X(\omega)$ in cell A is less than unity. Thus, in a pulsed radiofrequency field, the effect of the stimulating field sensed by the small cell is greater than the effect on the large cell. Consequently, a pulsed radiofrequency field can be applied which induces a reversible breakdown of the membrane of the small cell without irreversibly damaging the larger cell.

One embodiment of a device 10 for poration and/or fusion of biological particles is shown in FIG. 1. It includes a non-conducting container 13 for holding the solution 16 of biological particles 19. The container has a lightly concave bottom 22 so that biological particles 19 will congregate, under gravity, between the electrodes 25. The electrodes 25 are a pair of parallel or equidistant metal wires or metal bands made of nontoxic material, such as platinum or surgical stainless steel. The electrodes can be circular wire or large metal plates and can be in almost any shape or design. The container 13 has an access port 28 wherein biological particles 19 can be added or removed.

Figure 2A:
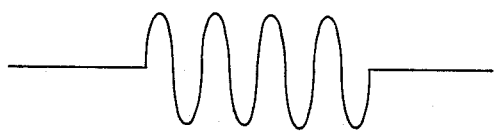
FIG. 2 is a graph of the radiofrequency (RF) pulses used in the present invention. 2A is a single frequency RF pulse, 2B is a RF pulse with a DC shift, 2C is an multiple frequency RF pulse, 2D is consecutive RF pulses of different frequencies and 2E is a low power AC field followed by a high power RF pulse followed by a low power AC field.
Figure 2B:
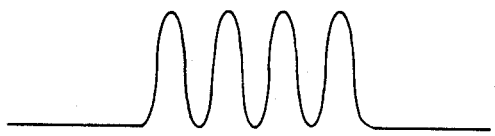
Figure 2C:
Figure 2D:
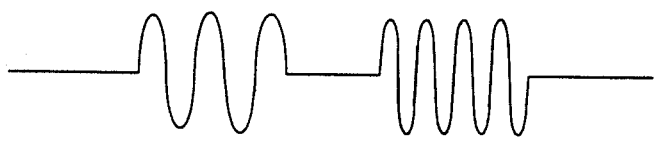
Figure 2E:
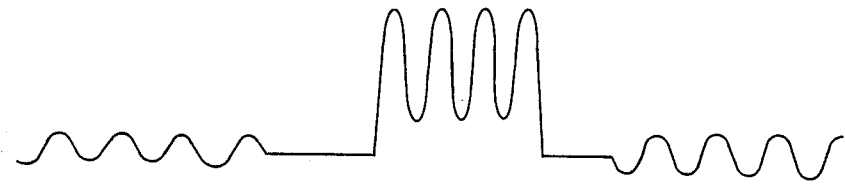

To induce cell-poration or cell-fusion, a high power function generator 31 generates one or several high power RF pulses which are applied through the pair of electrodes 25. The pulse shape can include one of those shown in FIG. 2. In FIG. 2A, the pulse is a pure RF oscillation with a single frequency. In FIG. 2B, the RF pulse consists of a single frequency pulse mixed with a DC component. In FIG. 2C, the RF pulse contains a mixture of multiple frequencies (in this example, two frequencies). In FIG. 2D, alternating pulses of different frequency are used. In the preferred embodiment, the pulse shown in FIG. 2B is used, because it allows the applied energy of the field to contain more than one Fourier component and is more efficient in inducing cell poration or fusion.

One skilled in the art will readily recognize that the parameters of the pulsed field are changed to accommodate the characteristics of the different biological samples. The radiofrequency within the pulse may vary over the complete radiofrequency range of 50 KHz to 500 MHz. Typically a value in the order of 0.1 to 10 MHz is used for the poration and/or fusion of biological cells.

The width of the pulse may vary from about 1 μsec to 10 msec. In the preferred embodiment approximately 20 to 200 μsec is used.

The field strength is controlled by varying the pulse amplitude. For fusion of cells the range of 1 to 15 kV/cm is employed. In the preferred embodiment pulses up to about 5 KV/cm are used.

In some instances such as the fusion of HL-60 cells, the maximum fusion yield is enhanced by applying multiple pulses.

The RF pulses used for cell-poration and cell-fusion are similar. The main difference is that in cell fusion, the cells need to congregate (be brought into close proximity) before the high power RF pulse is applied. Furthermore, the cells must be maintained in close proximity after application of the RF pulse. The above described device brought the cells together by gravitational congregation. An alternative, and more efficient method of cell aggregation is dielectrophoresis, where a continuous alternating current (AC) electric field is applied across the electrodes before and/or after the application of the high power RF pulse. The amplitude of this continuous AC field is typically in the range of 100 to 400 V/cm. Its frequency may vary from about 60 Hz to about 10 MHz. During cell fusion in the preferred embodiment the actual electric field applied across the electrodes will look like that shown in FIG. 2E.

Figure 3A:
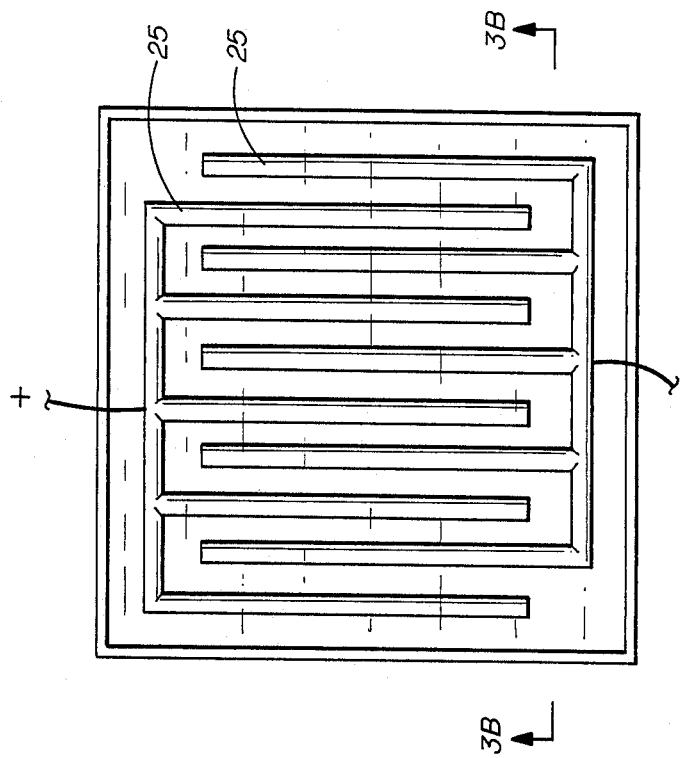
FIG. 3 is a schematic of one form of the present invention showing a large volume chamber for cell poration and/or cell fusion. 3A is a top view of the fusion chamber and 3B is a cross-sectional view showing the arrangement of electrodes in the chamber.
Figure 3B:
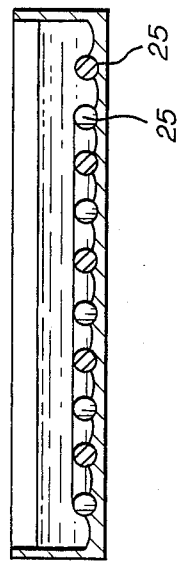

Another device for poration and/or fusion of larger volumes of cells is shown in FIG. 3. An array of equidistant electrodes 25 instead of a single pair of electrodes is used to apply the pulsed RF field.

Another preferred device 10 for cell poration and cell fusion is shown in FIG. 4. This device 10 is designed to allow observation of cell fusion under an optical microscope. This device is formed by two glass plates 34 separated by spacers 37 of approximately 0.3 mm thickness, with the cell suspension 19 sandwiched between the glass plates 34. In one embodiment thin glass plates such as cover slips are used. Electrodes 25 are two parallel platinum wires which are about 0.5 mm apart. The platinum wire electrodes 25 are connected to a high power function generator 31. The high power function generator can generate both alternating current electric fields and pulsed radiofrequency fields. An inlet tubing 41 and an outlet tubing 44 are used to insert and remove cells from the fusion chamber, that is the space between the electrodes.

Another embodiment of the present invention for cell poration and cell fusion is shown in FIG. 5. The purpose of this device is to porate or fuse a very large volume of suspended biological particles; including biological cells, vesicles, erythrocyte ghosts and liposomes. This device 10 is designed for ease in application, maintenance, and cleaning. The cell suspension is contained in a non-conducting cylindrical container 13. The electrode assembly 50 is attached to an insulating handle 47. To porate or fuse the suspended cells, the electrode assembly is lowered into the cell container 13 by manipulating the handle 47. The electrodes 25 are connected to the high power function generator 31 by a connection means 49. The AC field (cell fusion) and the high power RF pulses (cell poration and/or cell fusion) are then applied through the electrodes 25 in the electrode assembly 50.

In this device 10 the electrode assembly 50 is a vertical cylinder 53 and metal electrodes 25 are exposed at the side (i.e., the cylindrical surface). The cylinder can be any non-conducting material, for example, glass, plastic, or teflon. When the electrode assembly 50 is lowered into the cell container 13, the suspended cells 19 are displaced and form a thin layer of cell suspension 19 surrounding the electrode assembly 50. Thus, all cells are in close proximity of the electrodes. When an electrical potential is applied across the electrodes, the cells are exposed to the electric field.

Figure 6A:
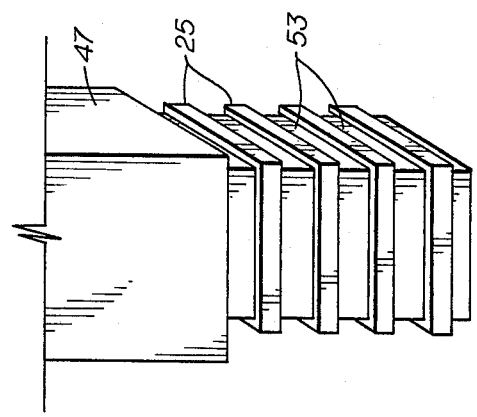
FIG. 6 is a schematic of a double helical design for the side-contact electrode assembly. 6A shows a elevational view of the helical design for the electrode assembly and 6B shows a side view of the same assembly.
Figure 6B:
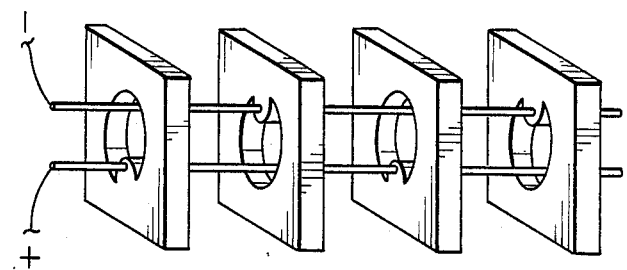

One design of the electrode assembly 50 is shown in FIG. 6. Two metal wires or bands are coiled to form a double helix electrode 25. The helices are identical in shape except one is positioned between the other. These two helice are attached to a cylindrical support 53. The spacing between these two helices 25 is kept constant. Thus, when an electrical potential is applied across the two metal wires, the amplitude of the electric field generated between the two helices is uniform along their entire length.

Figure 7A:
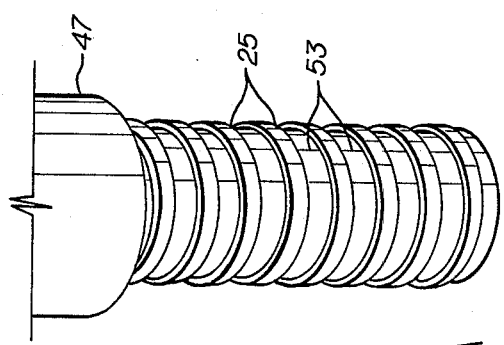
FIG. 7 is a schematic view of a segmented ring design for the side-contact electrode assembly. 7A shows an elevational view of the electrode assembly, 7B shows the connection of the electrode rings in the electrode assembly and 7C is a top view of a single electrode ring.
Figure 7B:
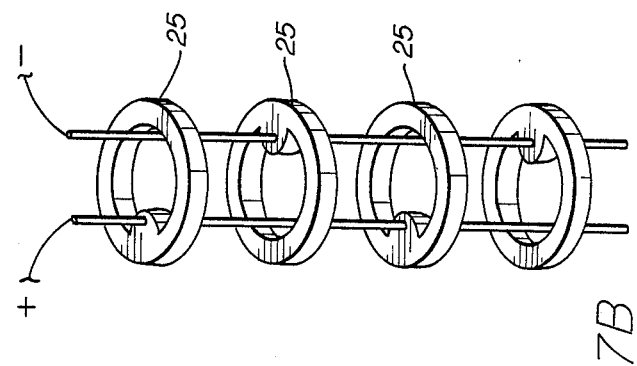
Figure 7C:
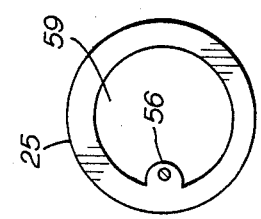

Another embodiment of the electrode assembly 50 for cell poration and cell fusion is shown in FIG. 7. Here the electrode 50 assembly is comprised of a stack of metal ring electrodes 25 separated by non-conducting insulating spacers 53 of fixed thickness. These ring electrodes 25 are connected together in an alternating fashion to form two sets of electrodes 25, each of which is then connected to the output terminals of the high power function generator. The rings have an attachment means 56 and a hollow area 59 for the passage of the wire to the alternate electrode 25.

Figure 8A:
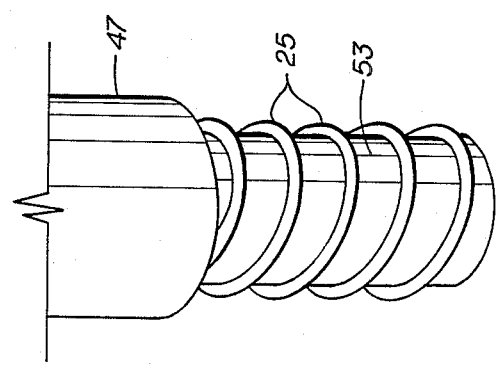
FIG. 8 is schematic of a rectangular electrode assembly for cell poration and cell fusion. 8A shows an elevational view of the electrode assembly and 8B shows the connection of the electrode squares in the electrode assembly.
Figure 8B:
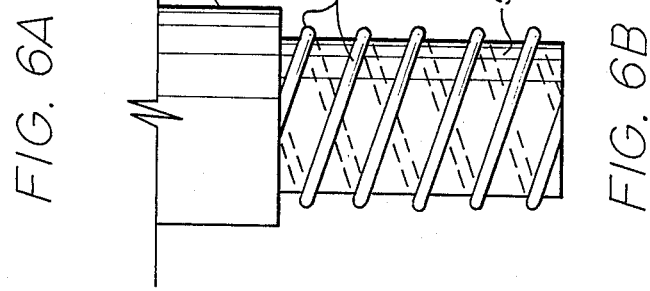
Figure 12C:
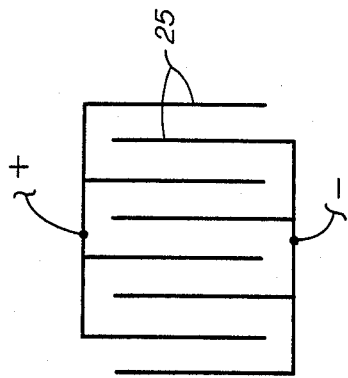
FIG. 12 is a schematic view of different designs for a bottom-contact electrode assembly. 12A is a top view of a square spiral assembly, 12B is a top view of a concentric square assembly, 12C is a top view of an interdigitating array assembly and 12D is a top view of a parallel plate assembly.
Figure 12B:
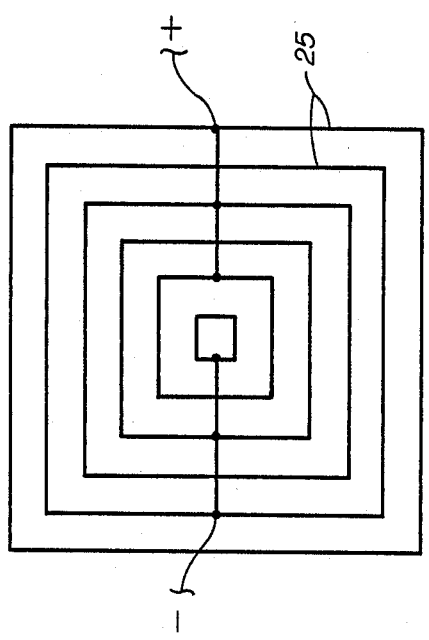
Figure 12A:
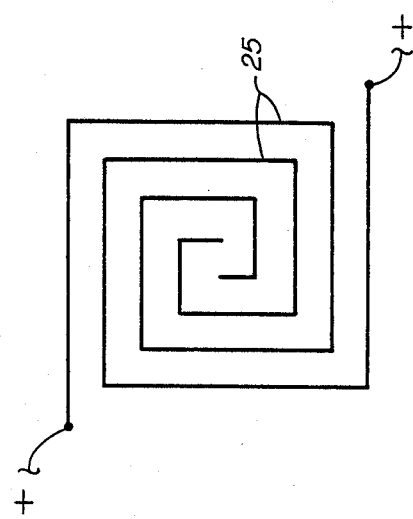
Figure 12D:
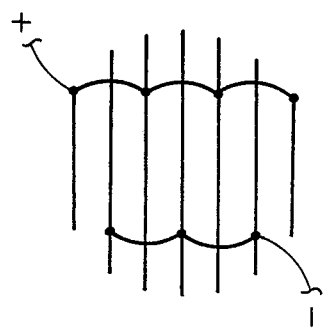

The electrodes 25 do not have to be circular, but can be any shape. Shapes which can be used include circular, rectangular as in FIG. 8 or eliptical.

Another embodiment for cell poration and cell fusion is shown in FIG. 9. The cell suspension 19 is contained in a non-conductive container 13. An electrode assembly 50 is attached to a handle 47 which can be used to manipulate the position of the electrodes. Unlike the previous devices, the electrodes of this embodiment are exposed at the bottom of the electrode assembly 50. This device is thus particularly useful in porating and/or fusing cultured cells that attach to the bottom of culture dishes.

One design of the bottom-contact electrode assembly 50 is shown in FIG. 10. The electrode assembly 50 consists of two spirals of metal bands, which serve as the "ground" (−) and "high voltage" (+) electrodes 25. The two spirals are positioned in such a way that the spacing between each spiral is maintained constant. The equal spacing arrangement ensures that an applied electric field across the two electrodes 25 is uniform in strength throughout the entire area covered by the electrode assembly.

In addition to the spiral design, other configurations including, multiple concentric rings, rectangular shapes, interdigitating arrays, parallel plates or eliptical shapes can be used (see FIGS. 11 and 12). The rings or shapes are connected in alternating fashion into two groups. One group of these rings or shapes are connected to the "ground" (−) terminal, while the other group of rings or shapes are connected to the "high voltage" (+) terminal of the high power function generator. The spacing between the rings or shapes is constant so that the strength of the electric field generated between the adjacent rings or shapes is uniform throughout the entire assembly. In the bottom-contact electrode assemblies the electrodes can be wires, plates or bands. In the preferred embodiment the width of the electrodes is greater than the depth of the cell suspension.

Excessive current is harmful to the cell because of the resulting thermal effects and pH changes. To avoid generating excessive current and the resulting effects during the application of the electric field, the suspension medium of the cells is usually a low ionic strength solution. Preferably it contains very low concentration of salts. A typical suspension medium may contain 1 mM of electrolyte including 0.4 mM Mg-acetate and 0.1 mM Ca-acetate. The medium is buffered and the pH maintained in the physiological range, for example, pH 7.5. Any buffer commonly used for biological uses purposes, for example, 1 mM HEPES (N-2-hydroxyethyl-piperazine-N'-2-ethane sulfonic acid) is adequate for cell poration and/or cell fusion. Non-electrolytes are added to maintain the osmolarity of the medium at about the osmolarity of extracellular fluid. In the preferred embodiment relatively high molecular weight, cell impermeable carbohydrates, such as sucrose and mannitol, are used as the non-electroyltes.

For some cells, a slightly higher ionic strength in the medium seems to improve the fusion yield. For example, human erythrocytes fuse easily in 30 mM Na-phosphate. Thus, the present method of fusion can use suspension medium with an ionic strength ranging from 0.1 mM to 100 mM depending on the cell type.

The present invention for cell poration and cell fusion has a variety of uses. Many biological active substances, including organic chemicals, inorganic chemicals, drugs, antibodies, proteins, hormones, growth factors, DNA, RNA, enzymes and radio- or fluorescent-labelled molecular probes normally cannot be readily taken up by cells. The present invention provides an effective method to transport these biological active substances into the cells. In one embodiment of the present invention cells can be temporarily permeabilized, that is porated, by applying high power RF pulses and the biological active substances then can enter the cells during this poration period. In another embodiment of the present invention, the biological active substances can be inserted into the cells by fusing the target cells with other biological particles which have been pre-loaded with the active substances. Such biological particles include liposomes and erythrocyte ghosts, which can be easily preloaded with desired substances using a standard osmotic shock and dialysis method. (Schlegel & Lieber *Cell Fusion* ed by A. E. Sowers Plenum Press (1987)). The target cells may be any cells which will receive the biological active substances and include isolated cells, egg cells, embroyonic cells, any primary or transformed cultured cells, or other cells in vitro.

Another embodiment involves the formation of new species by the fusion of cells. The suspended cells are selected from at least two different species. Thus after fusion a new species containing genetic material from both previous species is formed. One example of such a use of our fusion method is to fuse *N. tabacum* mesophyll protoplasts with mesophyll protoplasts of a kanamycin-resistant seed line of *N. plumbaoinifolia*, the resulting hybrids will develop into a new type of tabacum cells which are kanamycin-resistant.

Another embodiment employs a pulsed radiofrequency field to form hybridoma cells. In this instance the biological particles to be fused include antibody producing cells, for example, hyperimmunized mouse spleen cells and continuously dividing cancer cells, for example, myeloma cells. The resultan hybridoma cells can be used to produce monoclonal antibodies.

One example of the advantage that the present invention has over the direct current electro-fusion method is in the fusion of erythrocytes with a human lukemia cultured cell line, HL-60. This fusion was not obtainable using the DC pulse method. Such failure is probably due to the differences in cell size; erythrocytes are significantly smaller than HL-60 cells. Using the pulsed RF field, of the present invention results in the fusion of erythrocytes with HL-60 cells.

The fusion events were assayed by labelling the membranes of a small number of the suspended cells with a lipophyllic fluorescent dye, for example, 1,1',-dihexadecyl-3,3,3'',3'-tetramethylendocarbacyanine perchlorate. The cells were observed with a fluorescence microscope. When unlabelled cells fused with labelled cells, the dye was gradually transferred from the labelled cell to the unlabelled cell and eventually both cells became labelled. This transfer takes about a few minutes.

Up to 85% fusion yield is observed after a pulsed radiofrequency field is applied to erythrocytes. Under the same conditions the yield for HL-60 cells has been lower. One skilled in the art will recognize that the optimal condition may vary with different cell types, and that it is within the capabilities of one skilled in the art to easily alter the conditions to maximize the fusion yield.

One skilled in the art will readily appreciate the present invention is well adapted to carry out the objects and obtain the ends and advantages mentioned, as well as, those inherent therein. The devices, methods, procedures and techniques described herein are presently representative of the preferred embodiments, are intended to be exemplarily, and are not intended as limitations of the scope. Changes therein and other uses will occur to those skilled in the art which are encompassed within the spirit of the invention or defined by the scope of the appended claims.

What is claimed is:

1. A method for poration of biological particles, comprising the steps of:
   placing a plurality of biological particles in solution between electrodes; and
   applying a pulsed radiofrequency oscillating electrical field with sufficient strength to cause portition to occur.

2. The method of claim 1, wherein said biological particles are suspended cells in solution.

3. The method of claim 1, wherein said biological particles are attached cells in cell cultures.

4. The method of claim 1, wherein said pulsed radiofrequency field includes a frequency range of about 50 KHz to 500 MHz, a pulse width range of about 1 $\mu$sec to 10 msec, and a pulse amplitude range of about 1 KV/cm to 15 KV/cm.

5. The method of claim 1, wherein said pulsed radiofrequency oscillating field includes a frequency of about 0.1 to 10 MHz; a pulse width of about 20 to 200 $\mu$sec and a pulse amplitude of about 5 KV/cm.

6. The method of claim 1, wherein said frequency of said pulsed radiofrequency oscillating field is sufficient to cause the membrane of the biological particles to resonate.

7. The method of claim 1, wherein said pulsed radiofrequency oscillating field includes multifrequency components.

8. The method of claim 1, wherein said biological particles are selected from the group consisting of biological cells, vesicles, erythrocyte ghosts and liposomes.

9. A method for fusing biological particles, comprising the steps of:
   placing a plurality of biological particles in solution between electrodes;
   positioning said particles in close proximity; and
   fusing said biological particles by applying a pulsed radiofrequency oscillating electrical field across said electrodes.

10. The method of claim 9, wherein said positioning step includes placing suspended biological particles in a container which allows said biological particles to congregate.

11. The method of claim 9, wherein said positioning step includes:
   applying an alternating electrical field across said electrodes for bringing said particles into close proximity.

12. The method of claim 11, wherein said applying an alternating electrical field occurs before said porating step.

13. The method of claim 11, wherein said applying an alternating electrical field occurs after said porating step.

14. The method of claim 11, wherein said applying an alternating electrical field occurs before and after said porating step.

15. The method of claim 9, wherein said biological particles include a target cell and a particle preloaded with chemical agents or molecules for introducing chemical agents and molecules into cells.

16. The method of claim 15, wherein said particle preloaded with said chemical agents or molecules is selected from the group consisting of erythrocyte ghosts, liposomes, vesicles, isolated cells and cultured cells.

17. The method of claim 15, wherein said chemical agents and molecules are selected from the group consisting of antibodies, proteins, drugs, molecular probes, hormones, growth factors, DNA, RNA, enzymes, organic chemicals and inorganic chemicals.

18. The method of claim 9, wherein said biological particles include cells from at least two different species.

19. The method of claim 9, wherein said biological particles includes an antibody producing cell and a continuously dividing cancer cell.

20. The method of claims 9, wherein said biological particles includes hyperimmunized mouse spleen cells and myeloma cells.

21. The method of claim 9, wherein said biological particles includes cells of at least two different sizes.

22. A method for fusing biological particles, comprising the steps of:
   placing a plurality of biological particles in solution between electrodes, wherein said biological particles are selected from the group consisting of biological cells, vesicles, erythrocyte ghosts and liposomes;
   providing a low amplitude alternating electrical field across said electrodes for bringing said particles into close proximity by dielectrophoresis, wherein said electrical field has a frequency range of about 60 Hz to about 10 mega Hz and a field strength of about 100 to 400 V/cm.;
   applying a pulsed multifrequency radiofrequency oscillating electrical field across said electrodes for porating said particles, wherein said radiofrequency oscillating electrical field includes a frequency range of about 50 KHz to 500 KHz; a pulse width range of about 1 μsec to 10 msec, and a pulse amplitude range of about 1 KV/cm to 15 KV/cm; and
   providing an alternating electrical field across said electrodes for bringing said particles into close proximity for fusion, wherein said electrical field has a frequency range of about 60 Hz to about 10 mega Hz and a field strength of about 100 V/cm to 400 V/cm.

23. As a composition of matter, a hybridoma cell made by a method for fusing antibody producing cells with continuously dividing cancer cells, comprising the steps of:
   suspending antibody producing cells and cancer cells in solution between electrodes;
   providing an alternating electrical field wherein said electric field forms pearl chains by allowing the cells to move dielectrophoretically; and
   forming said hybridoma cell by applying a pulsed radiofrequency oscillating field across said electrodes.

24. The hybridoma cell of claim 23, wherein said antibody producing cells are hyperimmunized mouse spleen cells and the cancer cells are myeloma cells.

* * * * *

UNITED STATES PATENT AND TRADEMARK OFFICE
CERTIFICATE OF CORRECTION

PATENT NO. : 4,822,470

DATED : April 18, 1989

INVENTOR(S) : Donald C. Chang

It is certified that error appears in the above-identified patent and that said Letters Patent is hereby corrected as shown below:

Column 1, line 44, delete "Nos." and insert --No.--

Column 1, line 44, after "Sowers," insert --U. S. Pat. No. --

Column 1, line 45, after "Schoner," insert --U.S. Pat. No.--

Column 7, line 6, after "$V_c$" insert --.--

Column 11, line 59, delete "plumbaoinifolia" and insert
   --plumbaginifolia--

Column 12, line 44, delete "portition" and insert --poration--

Signed and Sealed this

Twenty-second Day of October, 1991

*Attest:*

HARRY F. MANBECK, JR.

*Attesting Officer*   *Commissioner of Patents and Trademarks*